United States Patent
Suzaki et al.

(10) Patent No.: US 6,614,919 B1
(45) Date of Patent: Sep. 2, 2003

(54) METHOD OF EXTRACTING IRIS REGION AND INDIVIDUAL IDENTIFICATION DEVICE

(75) Inventors: Masahiko Suzaki, Tokyo (JP); Yuji Kuno, Tokyo (JP)

(73) Assignee: Oki Electric Industry Co., Ltd., Tokyo (JP)

(*) Notice: Subject to any disclaimer, the term of this patent is extended or adjusted under 35 U.S.C. 154(b) by 0 days.

(21) Appl. No.: 09/469,223

(22) Filed: Dec. 22, 1999

(30) Foreign Application Priority Data

Dec. 25, 1998 (JP) .......................................... 10-368410

(51) Int. Cl.[7] ................................................ G06K 9/00
(52) U.S. Cl. ...................................... 382/117; 351/200
(58) Field of Search ............................ 382/117; 351/200

(56) References Cited

U.S. PATENT DOCUMENTS

| 5,291,560 A |   | 3/1994 | Daugman ................... 382/117 |
| 6,081,607 A | * | 6/2000 | Mori et al. .................. 340/5.8 |
| 6,144,754 A | * | 11/2000 | Okano et al. ................ 382/110 |
| 6,229,905 B1 | * | 5/2001 | Suzaki ........................ 382/116 |
| 6,424,727 B1 | * | 7/2002 | Musgrave et al. .......... 382/116 |

FOREIGN PATENT DOCUMENTS

| JP | 8-504979 | 5/1996 |
| WO | WO94/09446 | 4/1994 |

\* cited by examiner

Primary Examiner—Leo Boudreau
Assistant Examiner—Shefali Patel
(74) Attorney, Agent, or Firm—Venable LLP; Michael A. Sartori; Jeffrey W. Gluck

(57) ABSTRACT

An individual identification device and a method for extracting an iris region which can extract the iris region with high accuracy even if the shape of a pupil is not circular as in the case of a horse, cattle or the like. Contour lines of the pupil and an granula iridia are extracted from an image inputted. Part of a circle is applied to a contour line of the pupil and a radius of the contour line outside the iris region is estimated by an angle formed by two lines, one to connect both ends of the pupil and the other to pass the center of the circle. An iris circle is estimated by applying part of the circle to the contour line inside and outside the iris region.

17 Claims, 18 Drawing Sheets

(a)

(b)

(c)

DIRECTION OF CHANGES IN IRIS PATTERN

REGION WHERE AN ELLIPSE CANNOT BE APPLIED

CHANGES OF IRIS PATTERN BEING NOT SYSTEM OF POLAR COORDINATES (a) STATE OF NARROWING OF PUPIL (b) STATE OF DILATATION OF PUPIL (a) IMAGE INPUTTED (b) PUPIL RECTANGULAR IMAGE Ip (a)

(b)

(c)

(d)

(e)

(f)

(g)

(a)

(b)

NARROWED STATE OF PUPIL

DILATED STATE OF PUPIL d/D=0.8~1.0

(a)

(b)

01001 -------- 10110
00101 -------- 01110
01001 -------- 00110
         --------
11011 -------- 01110
01001 -------- 10110

LENGTH OF CODE LA (c)

(a)

(b)

```
010 ---------- 00
110 ---------- 11
101 ---------- 10
 | |            | |
 | |            | |         LENGTH OF CODE LR
 | |            | |
010 ---------- 01
000 ---------- 10
111 ========== 11
110           11
```

(c)

(a)

(b)

METHOD OF EXTRACTING IRIS REGION AND INDIVIDUAL IDENTIFICATION DEVICE

BACKGROUND OF THE INVENTION

1. Field of the Invention

The present invention relates to a method for extracting an iris region from an image of an eye of an animal or a human and more particularly to an individual identification device based on an iris code.

2. Description of the Related Art

Technologies for individual identification using an iris of an eye are conventionally used. The individual identification technology of this kind is disclosed, for example, in U.S. Pat. No. 5,291,560 or Japanese PCT Publication No. 8-504979. For individual identification, the conventional technology takes the following procedures:

1. A picture of an eye is taken by a camera or the like and a circle having its center in a pupil is applied to a border between the pupil and an iris and a border between the iris and a sclera. The circle is used as an internal border and an external border of the iris respectively.
2. A region between the borders of the iris is split into some ring-like bands and information about configuration of a pattern of each ring-like band is extracted by convolution technology using a 2-D Gabor filter and the extracted region is encoded by a value 0 (zero) or 1 in accordance with its amplitude.
3. The Hamming distance between an iris code registered in advance and an iris code produced using an inputted image is computed to authenticate individual identification.

In the conventional method, however, since the iris region is extracted on the precondition that the pupil is circular, in the case of an animal the pupil of which is elliptic, high accurate extraction of the iris region has been impossible.

FIG. 2 is an explanatory view of an eye of a human. FIG. 3 is an explanatory view of an eye of an animal. FIG. 3(a) shows an eye of a horse, (b) shows an eye of a dog and (c) shows an eye of a cat. As depicted in FIG. 3(a), contours of the pupil and the iris of the horse are not circular. Moreover, because there is a substance called a granula iridia on the contour line on the upper portion of the pupil, it is impossible to accurately extract the contour line of the pupil. Additionally, in the eyes of the animals as shown in FIG. 3(a) to (c), the border between the iris and the sclera hides behind an eyelid in many cases, so it is difficult to extract this contour line.

On the other hand, a method for producing iris codes by using the conventional method except the technique of approximation of the contour line in which an ellipse is used instead of the circle seemed possible; however, it has been proved that this method can not be applied to some sizes of the pupil where exact extraction of the contour line is impossible.

FIG. 4 is an explanatory view of states of dilatation and narrowing of the pupil. When an ellipse is applied to the pupil being narrowed as shown in FIG. 4(a), errors in the application occur in the vicinity of both ends of a long axis in particular, causing unstable setting of a system of coordinates and low accuracy in checking.

Moreover, the direction of movement of the iris pattern at the lower portion of the iris and at its both ends in response to changes of the pupil caused by brightness is as shown in FIG. 4 (the size of an arrow shows the amount of the movement). Therefore, when the iris pattern is expressed by a system of polar coordinates having its center in the pupil, the position of the iris pattern differs depending on the state of dilatation or narrowing of the pupil, causing disconformity of iris codes for identification.

As described above, the conventional individual identification presents a problem in that this method can not be employed for sufficiently accurate individual identification of animals such as a horse or cattle.

SUMMARY OF THE INVENTION

In view of the above, it is an object of the present invention to provide a method for accurately extracting an iris region even when a position of a pupil is changed.

According to a first aspect of the present invention, there is provided a method for extracting an iris region from an eye image obtained by taking a picture of an individual comprising steps of:

applying a circular arc to part of a border line between a pupil region and the iris region contained in the eye image; and setting a contour line outside the iris region on another circular arc having the same center as the above circular arc has.

In the foregoing, a preferable mode is one wherein a radius of the other circular arc being associated with a central angle of the circular arc applied for every individual is estimated.

Also, a preferable mode is one wherein the iris region is split in two directions, one being along the circular arc and the other being orthogonal to the circular arc and predetermined image processing is performed on each of split bands for encoding and obtaining two iris codes.

According to a second aspect of the present invention, there is provided a method for extracting an iris region from an eye image obtained by taking a picture of an individual comprising steps of:

applying an ellipse to a pupil region contained in the eye image; and estimating a radius of a border line outside the iris region based on a ratio of a long axis to a short axis of the ellipse.

According to a third aspect of the present invention, there is provided an individual identification device comprising:

a pupil contour extracting means to extract a contour of a pupil region from an eye image obtained by taking a picture of an individual;

a pupil circle/iris circle setting means to apply a circular arc to part of a contour of a pupil region extracted by the pupil contour extracting means and to obtain a border line outside the iris region based on a central angle of said circular arc;

an iris code producing means to produce an iris code of the iris region set by the pupil circle/iris circle setting means; and an iris code comparing means to compare the iris code produced by the iris code producing means with an iris code registered in advance and to use the result for individual identification of the eye image.

According to a fourth aspect of the present invention, there is provided an individual identification device comprising:

a pupil contour extracting means to extract a contour of a pupil region from an eye image obtained by taking a picture of an individual;

a pupil circle/iris circle setting means to apply a circular arc to part of a contour of a pupil region extracted by the pupil contour extracting means and to obtain a border line outside the iris region based on a central angle of the circular arc;

a first iris code producing means to produce the iris code of the iris region set by the pupil circle/iris circle setting means along the direction of a circumference of the iris region;

a second iris code producing means to produce the iris code of the iris region set by the pupil circle/iris circle setting means along the direction being orthogonal to the circumference; and an iris code comparing means to compare two iris codes produced by the first and second iris code producing means with an iris code registered in advance and to use the result for individual identification of the eye image.

Also, a preferable mode is one wherein the iris code comparing means outputs two degrees of dissimilarities between the produced iris code and the registered iris code, and there is provided a composite judging section to obtain a composite degree of dissimilarities from the two degrees of dissimilarities and to judge based on the composite degree of dissimilarities whether the produced iris-code conforms to the registered iris code.

BRIEF DESCRIPTION OF THE DRAWINGS

The above and other objects, advantages and features of the present invention will be more apparent from the following description taken in conjunction with the accompanying drawings in which.

DETAILED DESCRIPTION OF THE PREFERRED EMBODIMENTS

Best modes of carrying out the present invention will be described in further detail using various embodiments with reference to the accompanying drawings.

First Embodiment

Figure 5:
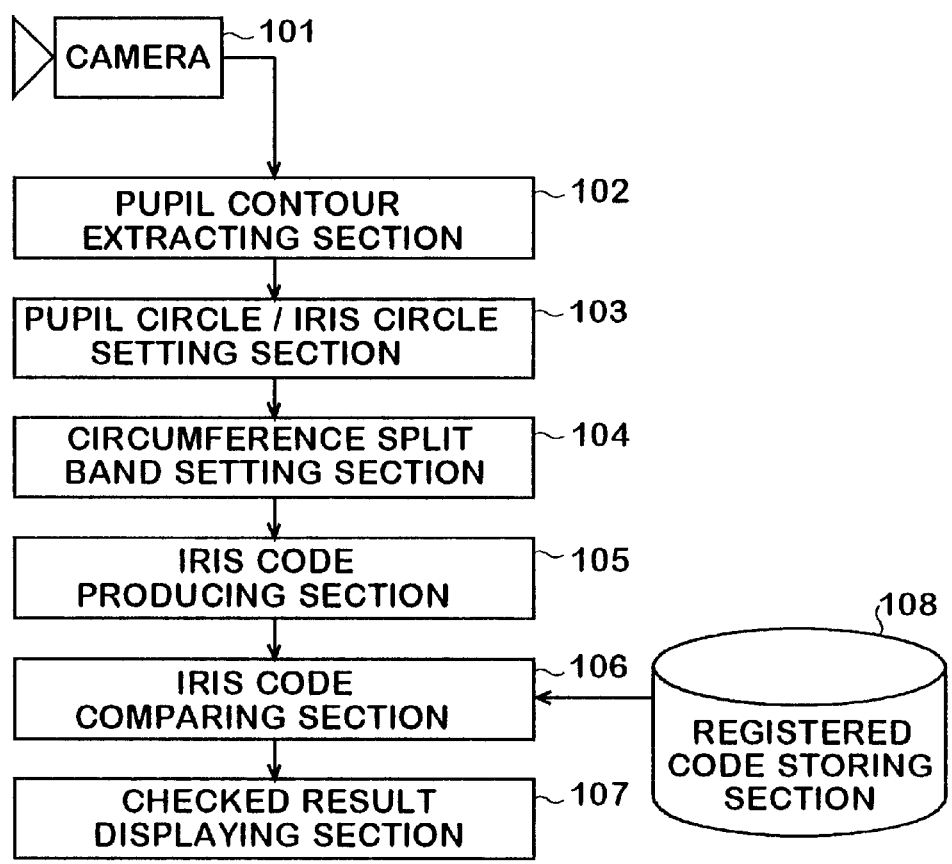
FIG. 5 is a block diagram explaining configurations of an individual identification device according to a first embodiment of the present invention.

Configurations and operations of an individual identification device of the present invention. FIG. 5 is a block diagram explaining configurations of the individual identification device according to a first embodiment of the present invention. As shown in FIG. 5, the individual identification device is comprised of a camera 101, a pupil contour extracting section 102, a pupil circle/iris circle setting section 103, a circumference split band setting section 104, an iris code producing section 105, an iris code comparing section 106, a checked result displaying section 107 and a registered code storing section 108.

The camera 101 is used to take a picture of an eye of an animal such as a horse, cattle or the like. The pupil contour extracting section 102 has a function of extracting a contour line of a pupil and an granula iridia from the picture taken by the camera 101. The pupil circle/iris circle setting section 103 has a function of applying a circular arc to the contour line of the pupil extracted by the pupil contour extracting section 102 and of estimating a circle representing contour lines of the iris and sclera based on the resulting circular arc.

The circumference split band setting section 104 is used to separate an internal contour line of the iris from an external contour line along a circumference and to obtain an image used for encoding. The iris code producing section 105 has a function of encoding the image obtained by the circumference split band setting section 104 by using a known frequency filter.

The iris code comparing section 106 has a function to perform an arithmetic operation to compare an iris code produced by the iris code producing section 105 with an iris code registered in advance. The checked result displaying section 107 is a device used to judge whether the image of the eye inputted on the basis of the comparison result obtained by the iris code comparing section 106 conforms to that of the eye of an animal registered and to display the result of the judgement. The registered code storing section 108 is used to store iris codes registered by steps taken by the camera 101 to the iris code producing section 105.

Figure 1:
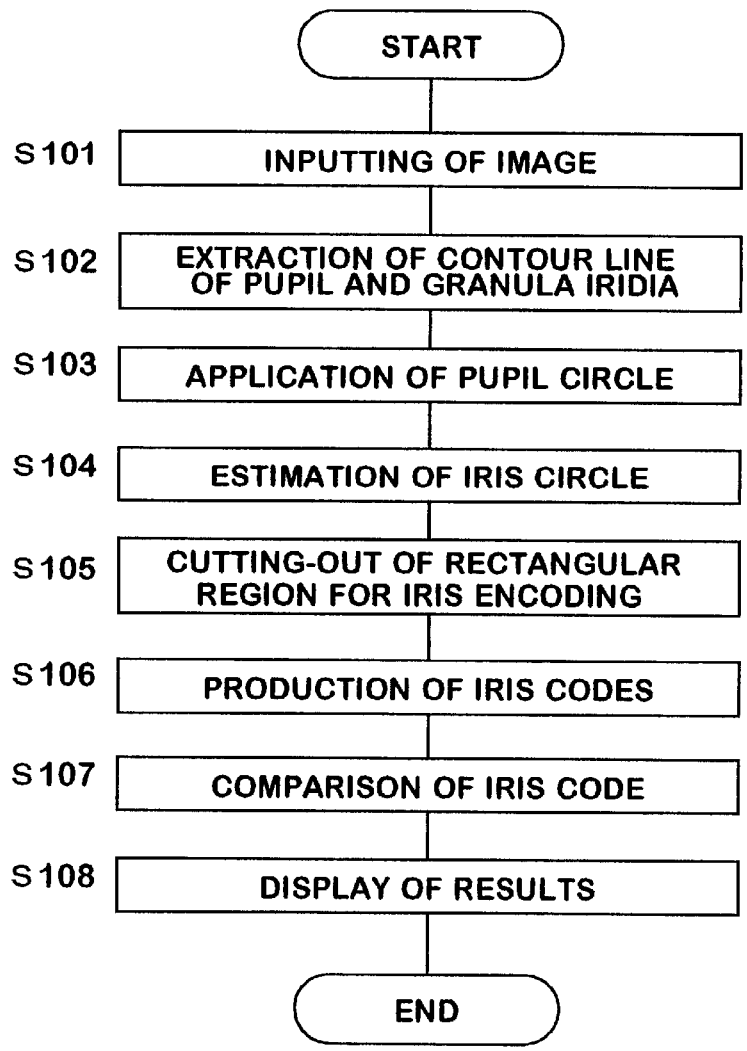
FIG. 1 is a flow chart explaining a method for extracting an iris region of the present invention.
Figure 2:
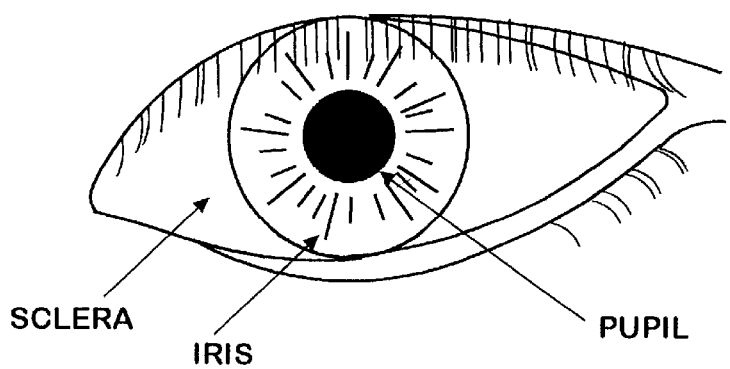
FIG. 2 is an explanatory view of an eye of a human.
Figure 3:
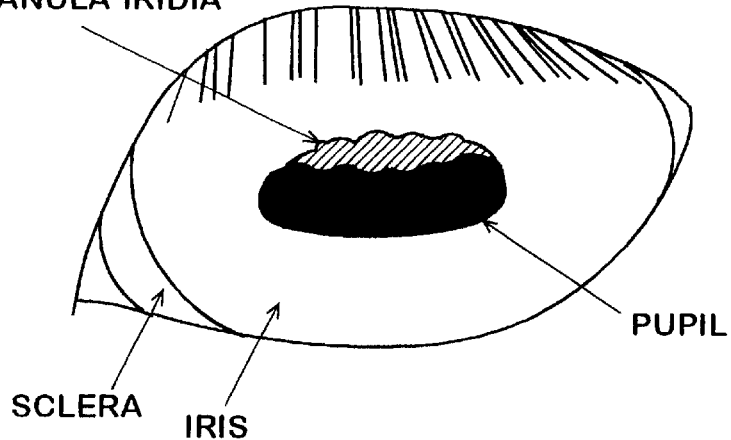
FIG. 3 is an explanatory view of an eye of an animal.
Figure 3:
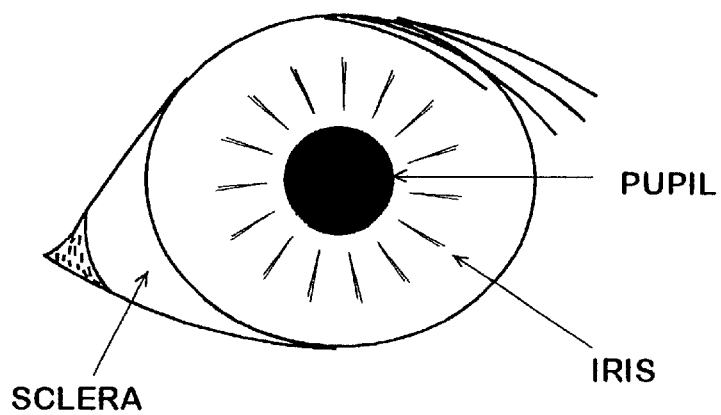
Figure 3:
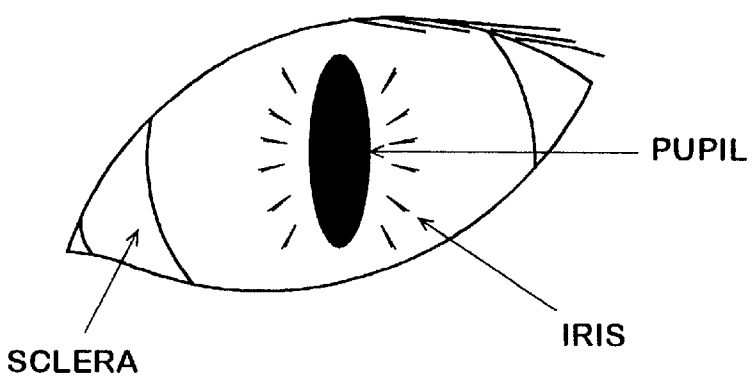
Figure 4:
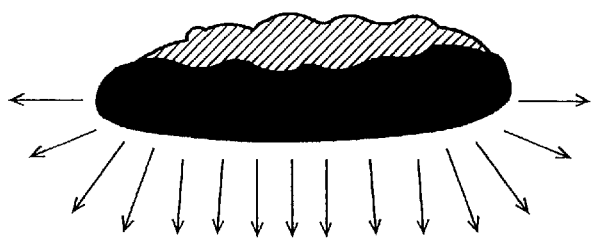
FIG. 4 is an explanatory view of states of dilatation and narrowing of a pupil.
Figure 4:
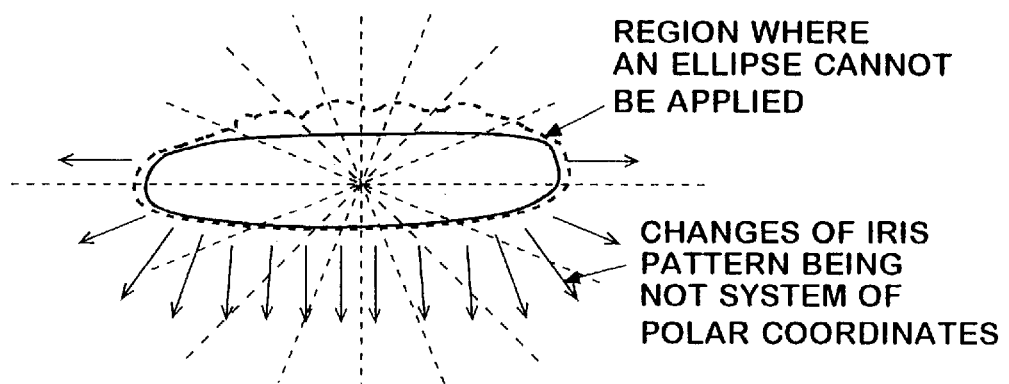
Figure 4:
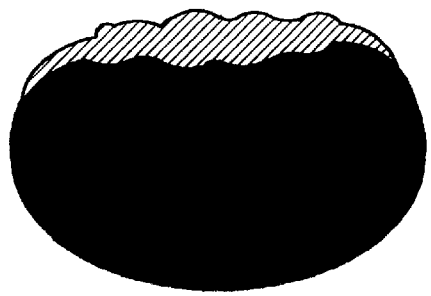

Operations of the individual identification device of the first embodiment by referring to FIG. 1. FIG. 1 is a flow chart explaining a method for extracting the iris region of the present invention.

In Step S101, the image of the eye taken by the camera 101 is digitized through A/D (Analog/Digital) conversion and is stored in a memory of a computer (not shown) of the pupil contour extracting section 102.

In Step S102, the contour line of the pupil and the granula iridia are extracted by the pupil contour extracting section 102 by a binarization process of the image obtained.

In Step S103, part of a circle (i.e., circular arc) is applied to the contour line positioned under the pupil by the pupil circle/iris circle setting section 103. This circle is hereinafter referred to as a "pupil circle".

In Step S104, a circle of the contour surrounding the iris is estimated by the pupil circle/iris circle setting section 103 on the basis of the pupil circle. This circle is hereinafter referred to as an "iris circle".

In Step S105, a rectangular region to be encoded is cut out by the circumference split band setting section 104.

In Step S106, the rectangular region is split by the circumference split band setting section 104 and each split band is encoded by the iris code producing section 105 using a 2-D Gabor filter or the like.

In Step S107, the iris code produced by processing provided by steps up to Step S106 is compared, by the iris code comparing section, with that in advance registered to authenticate individual identification.

In Step S108, a result from Step S107 is displayed by the checked result displaying section 107.

More detailed description of the processing performed at each step shown above by referring to FIG. 1.

(1) Processing of Extraction of Contour Line of Pupil and Granula Iridia (Step S102)

Figure 6:
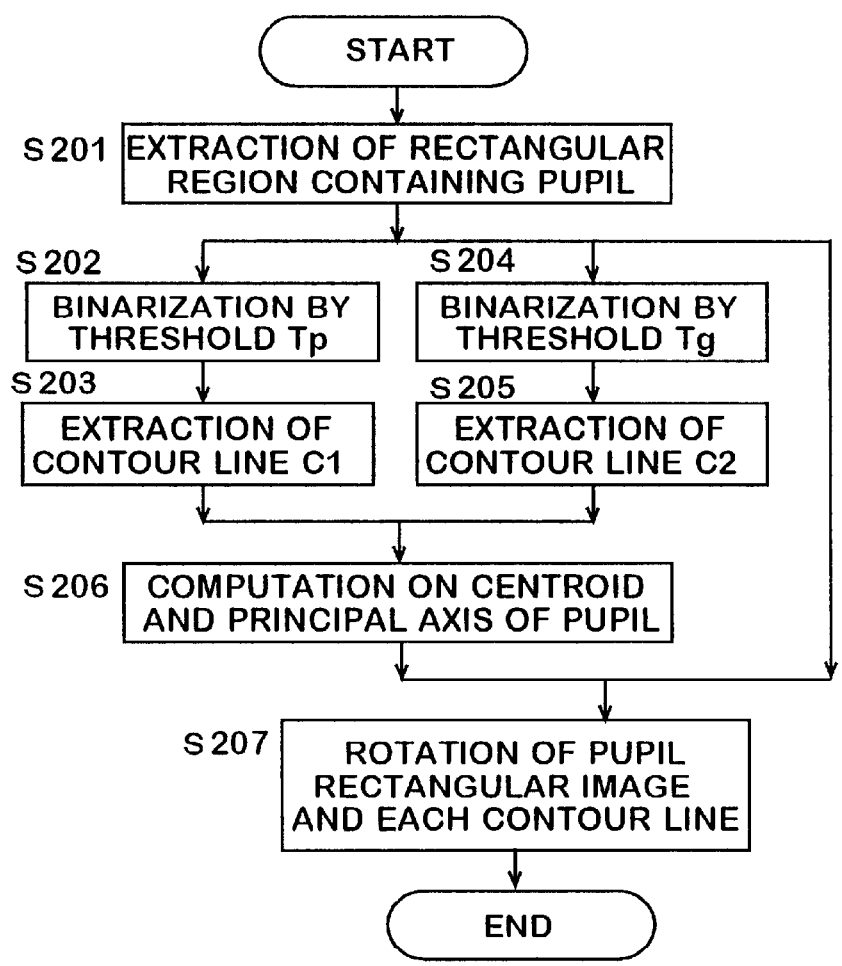
FIG. 6 is a flow chart showing the processing of extraction of the contour line of the granula iridia of the first embodiment.

FIG. 6 is a flow chart showing the processing of extraction of the contour line of the granula iridia provided in Step S102.

First, a rectangular region containing the pupil and granula iridia regions is extracted from the image inputted (Step S201). The extraction is made assuming that the pupil shows the darkest region in the image of the eye which exists in the vicinity of a center of the image. The image is binarized using an appropriate threshold value T and the region of the pupil existing in the vicinity of the center of the image among regions being darker than that indicated by the threshold value is extracted.

Figure 7:
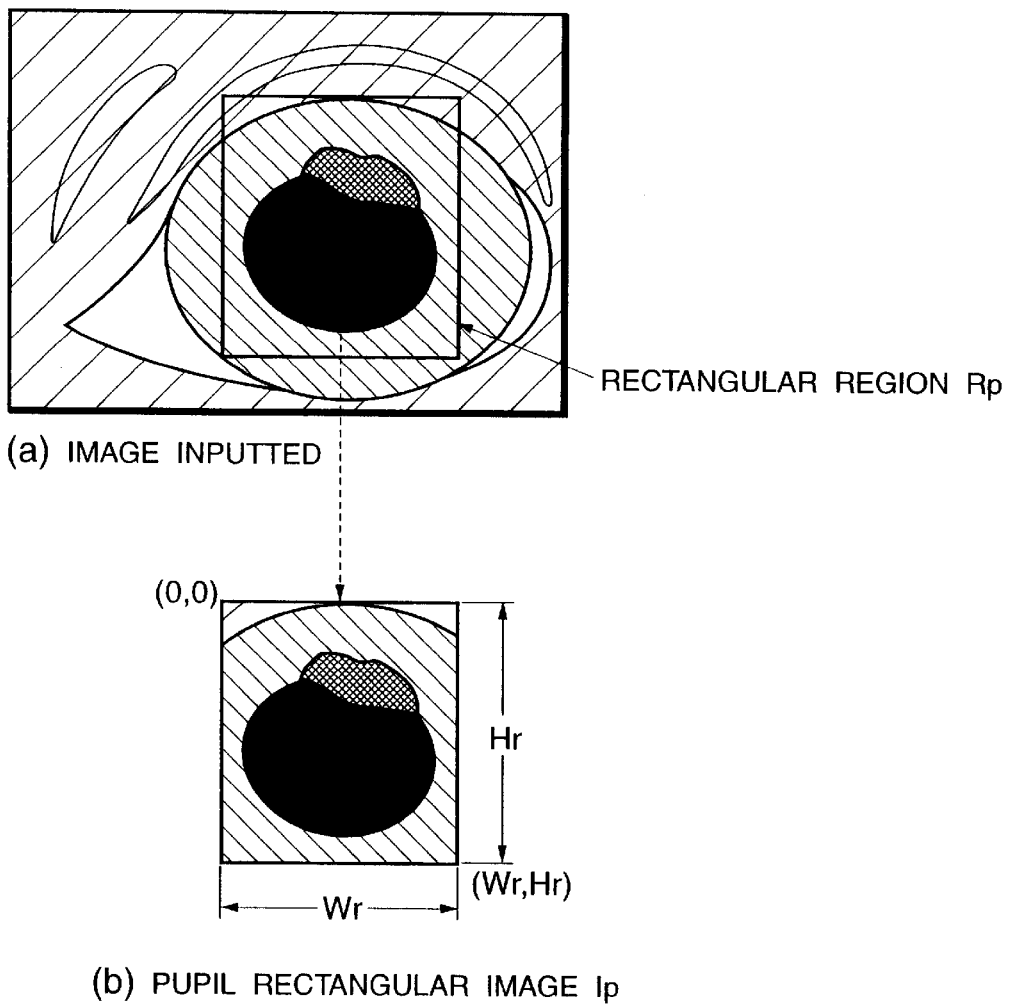
FIG. 7 is a schematic diagram explaining the extraction of the rectangular region including the pupil region of the first embodiment.

FIG. 7 is a schematic diagram explaining the extraction of the rectangular region including the pupil region. In FIG. 7(a), Rp represents a rectangular region containing the pupil region to be extracted. A sufficient margin is given to the region showing only the pupil so that a region of the granula iridia is also contained in the rectangular region Rp in which Wr and Hr represent its width and height respectively. The size of the margin may be fixed or may be changed depending on a size of the pupil extracted. Thus, the image obtained by cutting out the rectangular region from the inputted image is hereinafter referred to as a "pupil rectangular image Ip" represented by a system of coordinates in which coordinates (0,0) and (Wr, Hr) are provided at the upper and lower left points of the image respectively.

Figure 8:
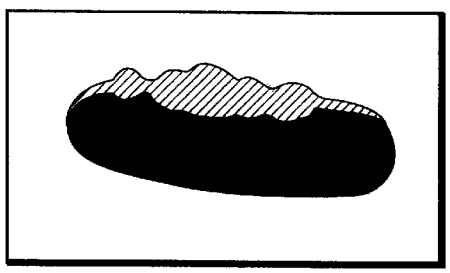
FIG. 8 shows examples of processes of binarizing the pupil rectangular image and of extracting its contour lines according to the first embodiment of the present invention.
Figure 8:
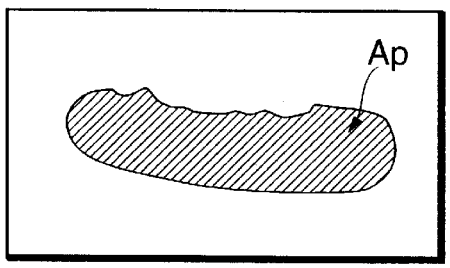
Figure 8:
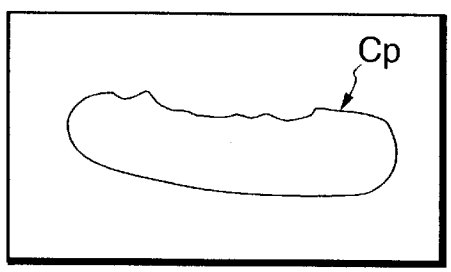
Figure 8:
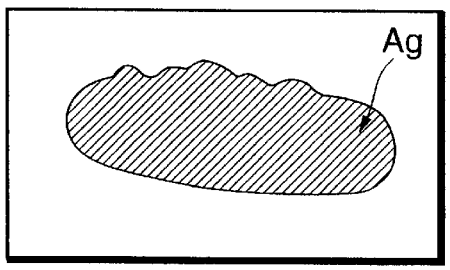
Figure 8:
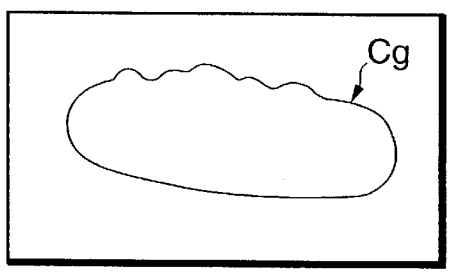
Figure 8:
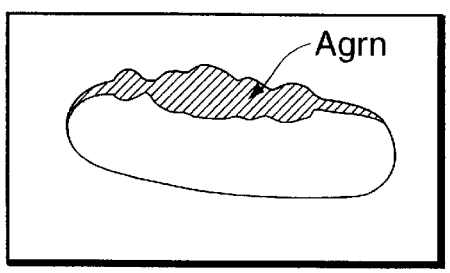
Figure 8:
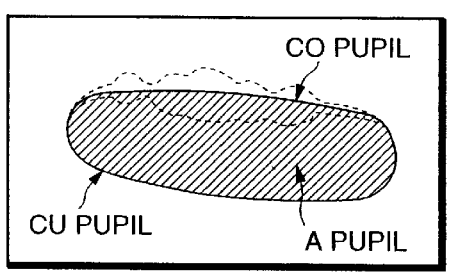

In the pupil rectangular image Ip, the pupil region has the lowest average density, the granula iridia region has the next lowest and the iris region has the next lower. Then, threshold values Tp and Tg are set under next conditions:

Dp<Tp<Dg<Tg<Di where Dp represents the average density of the pupil region, Dg represents the average density of the granula iridia region and Di represents the average density of the iris region. The low density value means that any region is dark. FIGS. 8 shows examples of processes of binarizing the pupil rectangular image and of extracting its contour lines according to the embodiment of the present invention.

First, the pupil rectangular image shown in FIG. 8(a) is binarized by using threshold value Tp (Step S202 in FIG. 6). The region being darker than that indicated by the threshold value Tp as shown in FIG. 8(b) contains only the image of the pupil, which is hereafter referred to as a region "Ap". The contour line of the region Ap constitutes the contour line of the pupil and the contour line below the granula iridia (i.e., a border between the pupil and the granula iridia) to be extracted (Step S203 in FIG. 6), which is hereafter referred to as a contour line "Cp" (see FIG. 8(c)).

Next, the pupil rectangular image is binarized by using threshold value Tg (Step S204). The region being darker than that indicated by the threshold Tg is a region where the regions of the pupil and granula iridia, which is hereafter referred to as a region "Ag". The contour line of the region Ag constitutes the contour line of the pupil and contour line above the granula iridia (i.e., a border between the iris and the granula iridia) (Step S205), which is hereafter referred to as a contour line "Cg" (see FIG. 8(e)).

The region disposed between the contour line Cp and Cg is a region Agrn of the granula iridia as shown in FIG. 8(f). Moreover, in the case of an eye of a horse, because the granula iridia is positioned at the upper portion of the pupil, lower half portions of the contour lines Cp and Cg overlap. Therefore, lower half portions of the contour lines Cp and Cg are defined to be a contour line "CUpupil" of the lower part of the pupil. The line passing between the contour lines Cp and Cg is defined to be a contour line "COpupil" of the upper part of the pupil. The region surrounded by the contour lines CUpupil and COpupil is defined to be a pupil region "Apupil" as shown in FIG. 8(g).

Next, a centroid and main axis (i.e., a straight line passing through the most extended region of the pupil) of the pupil are obtained by using a principal component analysis or the like (Step S206).

Figure 9:
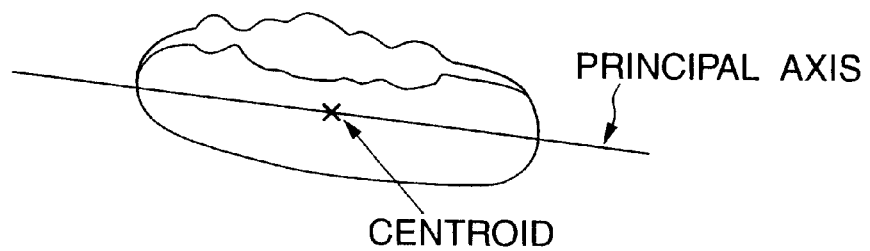
FIG. 9 is an explanatory view of operations for correcting the inclination of the pupil of the first embodiment.
Figure 9:
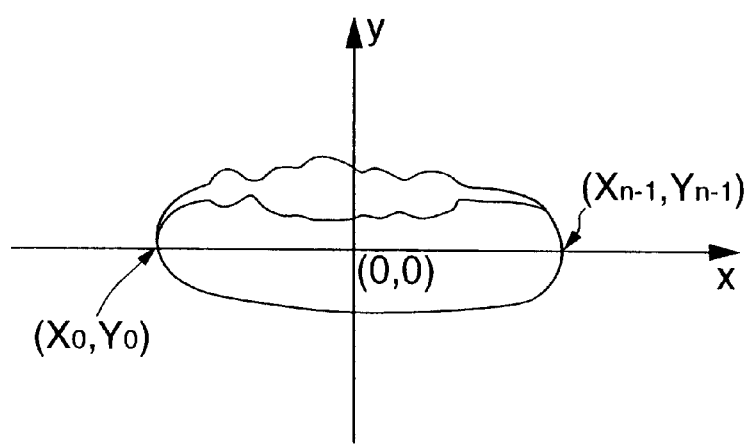

Then, the inclination of the pupil is corrected (Step S207). FIG. 9 is an explanatory view of operations for correcting the inclination of the pupil. As depicted in FIG. 9(a), the principal axis is indicated by a straight line passing through the most extended region of the pupil. The pupil rectangular image and the contour lines Cp and Cg are rotated round the center of the centroid of the pupil so that the principal axis is horizontal and coordinates x-y is newly set with the centroid of the pupil being defined as an origin (0,0) and the principal axis being defined as an x axis (Step S207) as shown in FIG. 9(b).

Moreover, methods for extracting contour lines of the pupil and granula iridia as disclosed in, for example, Japanese Patent Application No. 9-073190 and/or No. 9-343841 may be used in addition to methods described above.

(2) Description of Processing of Applying Pupil Circle (Step S103)

A circular arc having a center on a y-axis of the x–y coordinates set above is applied to the contour line of the lower part of the pupil.

As shown in FIG. 9(b), a set of picture elements constituting the contour line CUpupil of the lower part of the pupil obtained by rotating the pupil rectangular image and contour lines so that the principal axis is horizontal is given by the following equation:

$$CUpupil=\{(X0, Y0), (X1, Y1), \ldots (Xn-1, Yn-1)\}$$

where "n" represents the number of points constituting a contour line and Xi<X1+1 is for 0≦i<n.

While the pupil contracts, since it is impossible to approximate both a center of the contour line at the lower portion of the pupil and an area near to both ends of the pupil by using the same circular arc, the circular arc is applied to an area from which the area near to both ends of the pupil is cut. Five to 10 percent of the length of the right and left distances (defined to be "Lp") of both ends of the pupil is cut. The number of picture elements to be cut is defined as "m" for one end (i.e., "2m" for one pupil including both ends).

Figure 10:
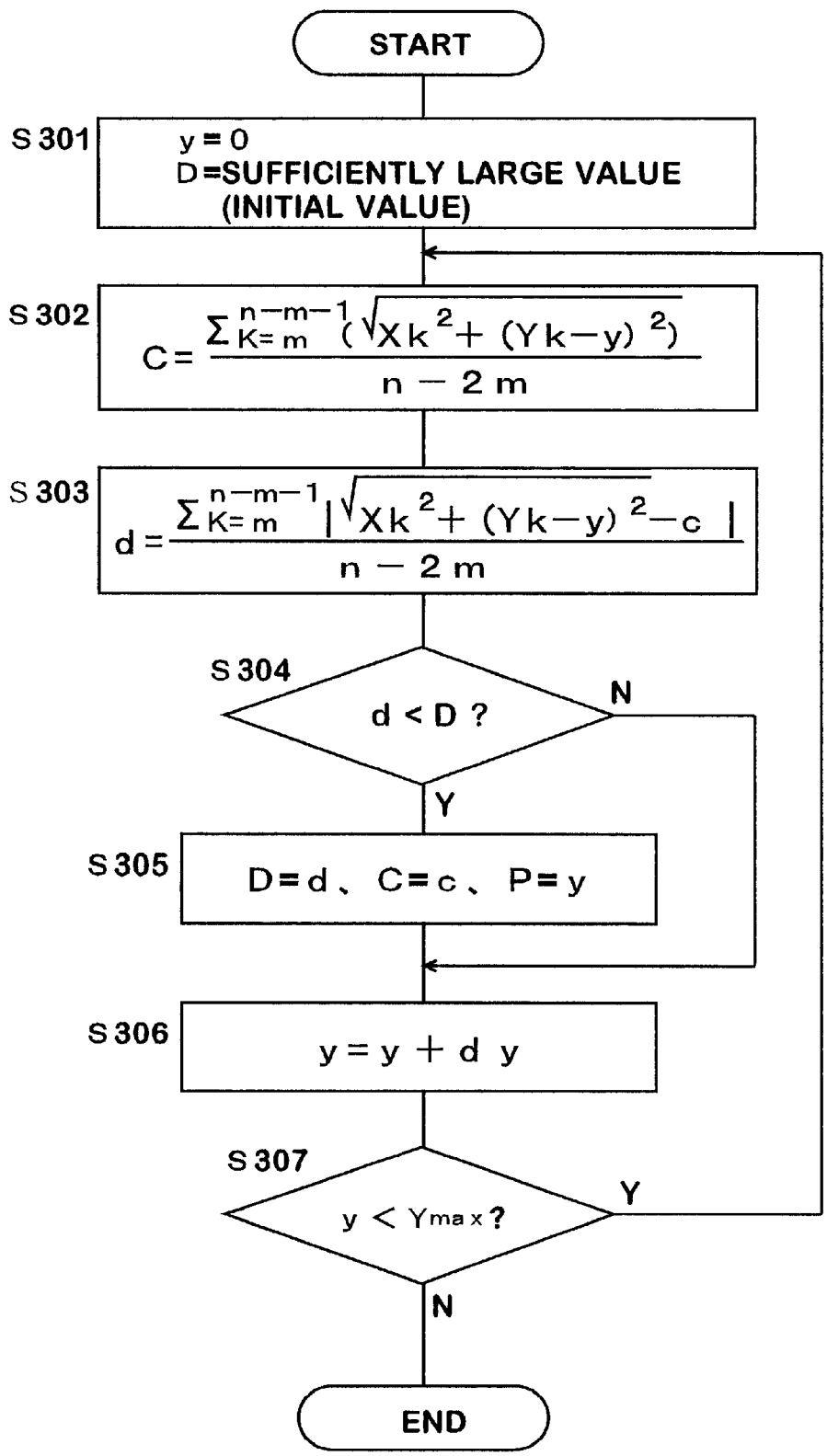
FIG. 10 is a flow chart explaining processes of the application of a circular arc of the first embodiment.

The application of the circular arc to the contour at the lower portion of the pupil is performed in a manner described below. FIG. 10 is a flow chart explaining processes of the application of a circular arc.

First, a procedure is started as y=0 and a sufficiently big value is given to "D" (this represents an error value to be finally obtained) (Step S301). Next, an average radius "c" to be obtained from the contour line with a center of a circle being set to (0, y) is calculated (Step S302). Then, an average error "d" is computed (S303). Whether the error d is smaller than D (error value) or not is judged (Step S304). If the judgement in Step S304 shows that d<D, the error value D is defined as an error "d" at the time, the radius C is defined as the average radius "c" at the time and a coordinate P on the y axis of the center of the circular arc is defined as a coordinate value "y" at the time (Step S305).

The value y is increased by dy (Step S306) and whether the value y is smaller than Ymax (Step S307) or not is judged. If so, the procedure is returned back to Step S302 and the above procedures are repeated. However, dy and Ymax are positive constants and dy represents an increment of y to the maximum value Ymax of y determined in advance based on the initial setting of y=0.

Thus, the radius c and error d of the circular arc from the state y=0 to the state y=Ymax are obtained and the coordinate value y having the least error d is defined as a center P of the circular arc and the radius c is defined as a radius C. These P and C are used as a y coordinate of a radius and a center of a circular arc to be applied to the contour at the lower portion of the pupil.

Figure 11:
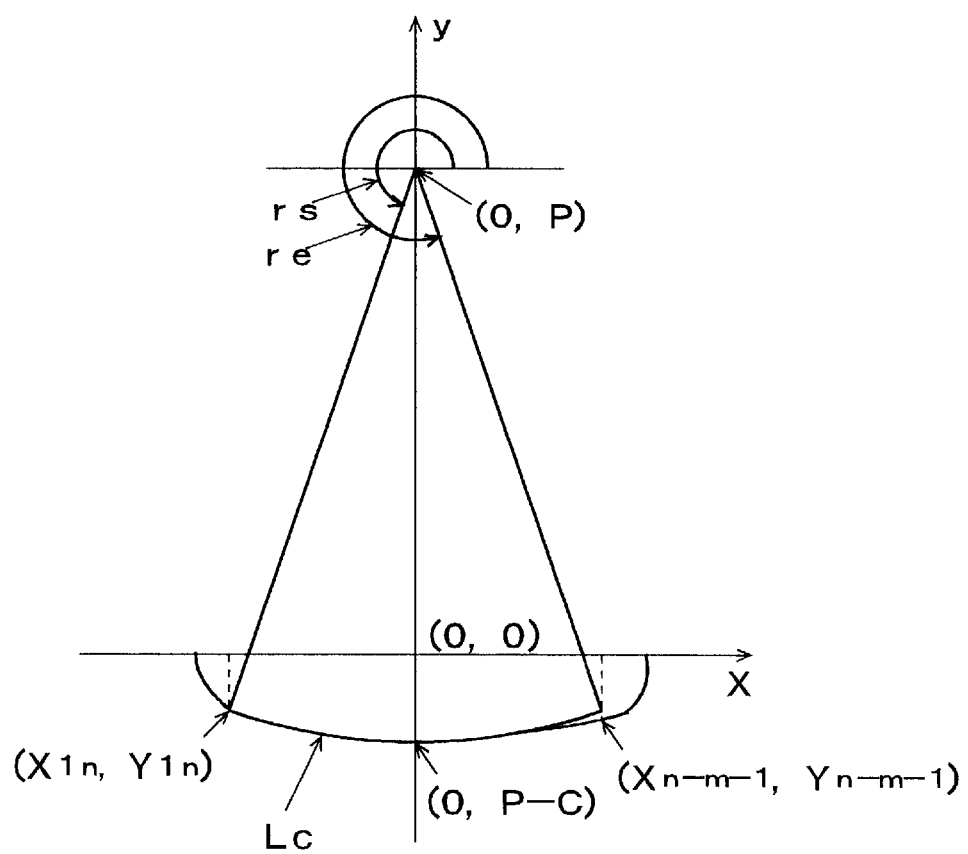
FIG. 11 is a view explaining the application of the circular arc to the pupil of the first embodiment.

FIG. 11 is a view explaining the application of the circular arc to the pupil. As shown in FIG. 11, an equation of a circle containing an circular arc is given as follows:

$$x^2+(y-p)^2=C^2$$

The relation of angles of the circular arc and its length is expressed by the following equation:

$$rs=\pi-re=\arccos(Xm/C)$$

$$Lc=2\pi C\times\{(re-rs)/2\pi\}=C\times(re-rs)$$

where rs and re (=$\pi$−rs) represent angles for a start and end of the circular arc corresponding to a contour line obtained by this approximation and Lc represents the length (diameter) of the circular arc.

In addition to methods described above, other methods for applying a circular arc including Hough Transform method or the like may be used.

(3) Description of Processing of Estimating Iris Circle (Step S104)

As described in the prior art, most of the contour outside an iris of an animal such as a horse or cattle hides behind its eyelid in many cases. Because of this, when its contour is extracted from the image, the result of the extraction becomes unstable, which may cause low recognition accuracy.

If, therefore, the degree of dilatation or narrowing of the pupil is found, it is possible to estimate the position of the contour line outside the iris. Moreover, when the circular arc is applied to the pupil of the same horse, its central angle becomes large while the pupil dilates. On the other hand, it becomes small while the pupil narrows. This means that the degree of dilatation or narrowing of the pupil (hereafter referred to as a "degree of opening of the pupil") can be represented by the size of the central angle.

Figure 12:
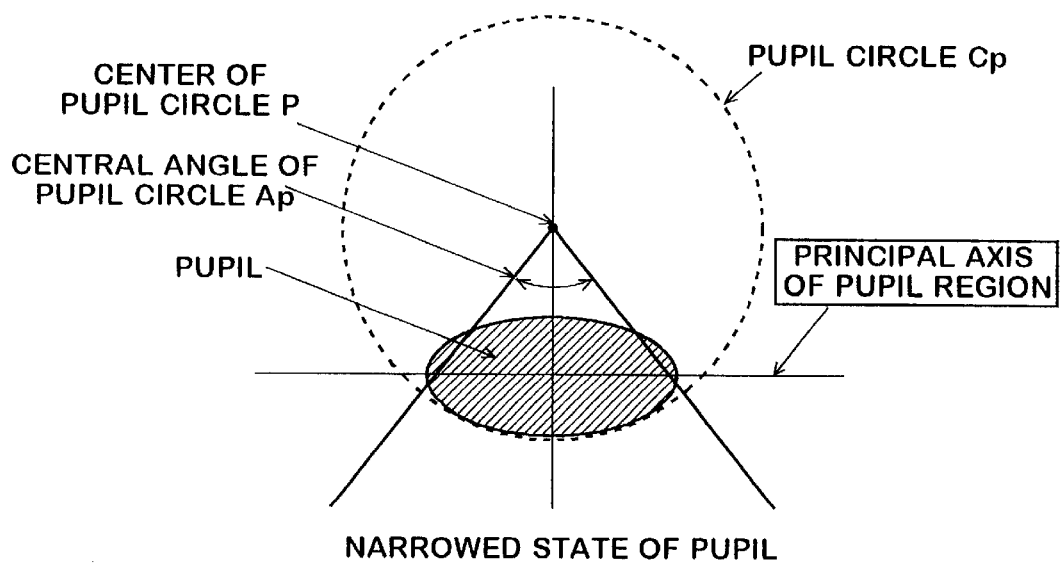
FIG. 12 is a view explaining a "pupil circle" in states of dilatation and narrowing of the pupil in the same horse of the first embodiment.
Figure 12:
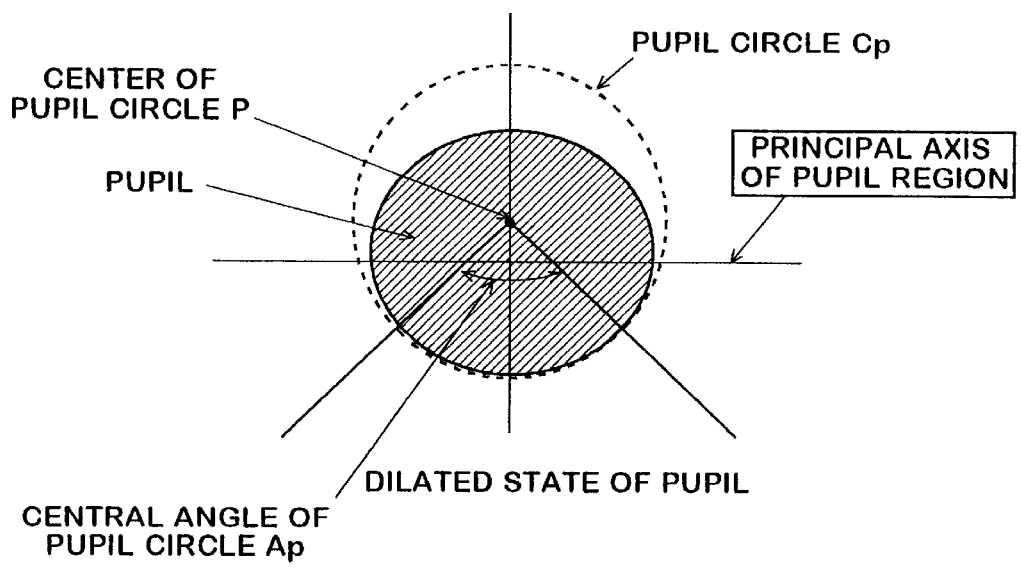

FIG. 12 is a view explaining a "pupil circle" in states of dilatation and narrowing of the pupil in the same horse. As is depicted in FIG. 12, the central angle Ap of the pupil is small while the pupil narrows and it is large while the pupil dilates.

Figure 13:
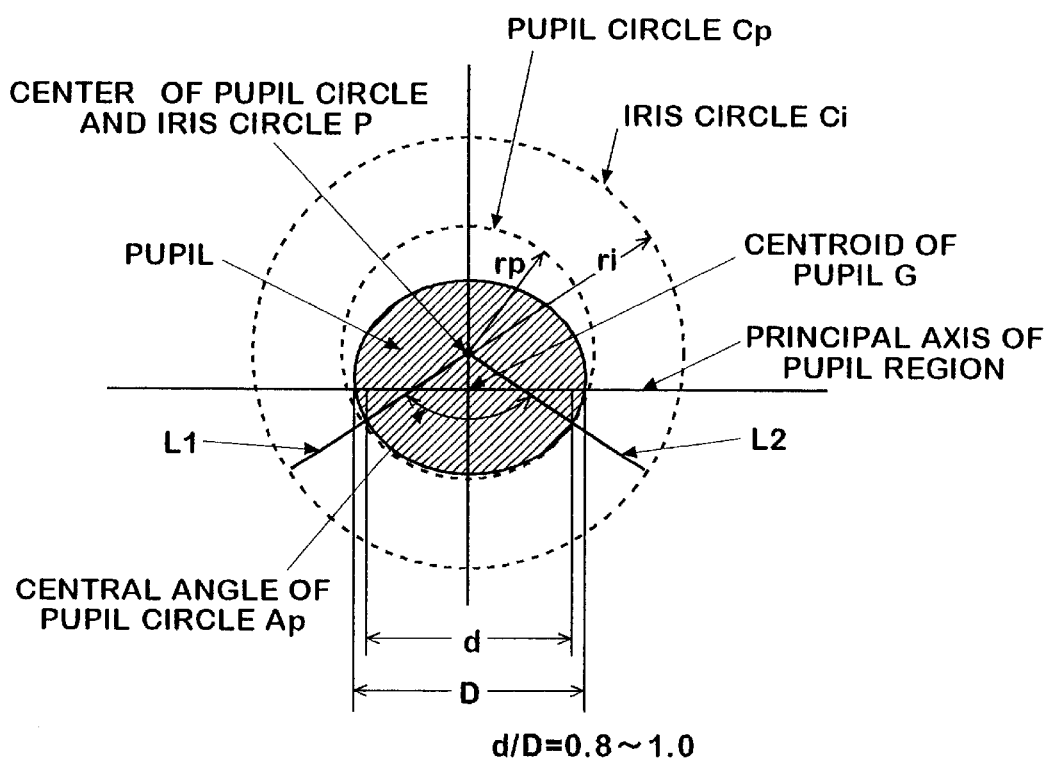
FIG. 13 is a view explaining a system of coordinates of a circle extracted by the process of applying the pupil circle of the first embodiment.

Examples of concrete estimation of an iris circle are described below. FIG. 13 is a view explaining a system of coordinates of a circle extracted by the processing of applying the pupil circle (Step S103). In FIG. 13, the central angle of the circular arc on the pupil circle Cp is defined to be Ap and is hereinafter referred to as a "pupil central angle". The radius of the pupil circle Cp is defined to be "rp". The radius of the iris circle Ci to be estimated is defined to be "ri". The center and central angle of the pupil circle and the iris circle are the same.

Let it be assumed that the pupil circle of a horse is extracted in accordance with methods (Step S101 to S103) shown in FIG. 1. At this point, a ratio of the radius rp of the pupil circle and the radius ri of the iris circle to the central angle Ap of the pupil is determined (ratio IP=ri/rp). This determination is performed on the various degree of opening of the pupil of more than one horse and a relation between the central angle Ap and the ratio IP can be graphed. Based on the result of the determination, an approximation formula "Ratio IP (Ap)" showing a relation between Ap and ratio IP is solved.

The approximation formula Ratio IP (Ap) is adapted to output a ratio of the radius of the pupil circle Cp to that of the iris circle Ci when the central angle Ap of the pupil is inputted at a state and, because the radius rp of the pupil circle is known, the radius ri of the iris circle can be calculated accordingly as follows:

$$ri=\text{Ratio } IP(Ap)\times rp$$

The estimation of the iris circle can be made by a method other than described above, i.e., the iris circle can be estimated by applying an ellipse to the pupil and by the radius of the contour line outside the iris on the basis of a ratio of a length of a long axis of the ellipse to that of a short axis. This method also allow highly accurate extraction of the iris region in accordance with the states of dilatation or narrowing of the pupil.

Thus, according to the method for extracting the iris region of the present invention, to extract the iris region from an image of an eye, since the extraction is performed by applying part of the circle to the contour line inside and outside the iris region, even if a shape of the pupil is not circular as in the case of a horse or cattle, the iris region can be extracted with high accuracy.

Moreover, according to the method of the present invention, since the contour line outside the iris region is adapted to be estimated on the basis of the shape of the pupil, highly accurate extraction of the iris region in accordance with the states of dilatation or narrowing of the pupil is made possible.

Furthermore, since the radius of the contour line outside the iris region is adapted to be estimated on the basis of an angle formed by two straight lines, one to connect both ends of the pupil and the other to pass the center of the circle, the contour line outside the iris region can be more exactly obtained and the iris region can be extracted with high accuracy.

(4) Description of Processing of Obtaining Rectangular Region for Iris Encoding (Step S105)

Figure 14:
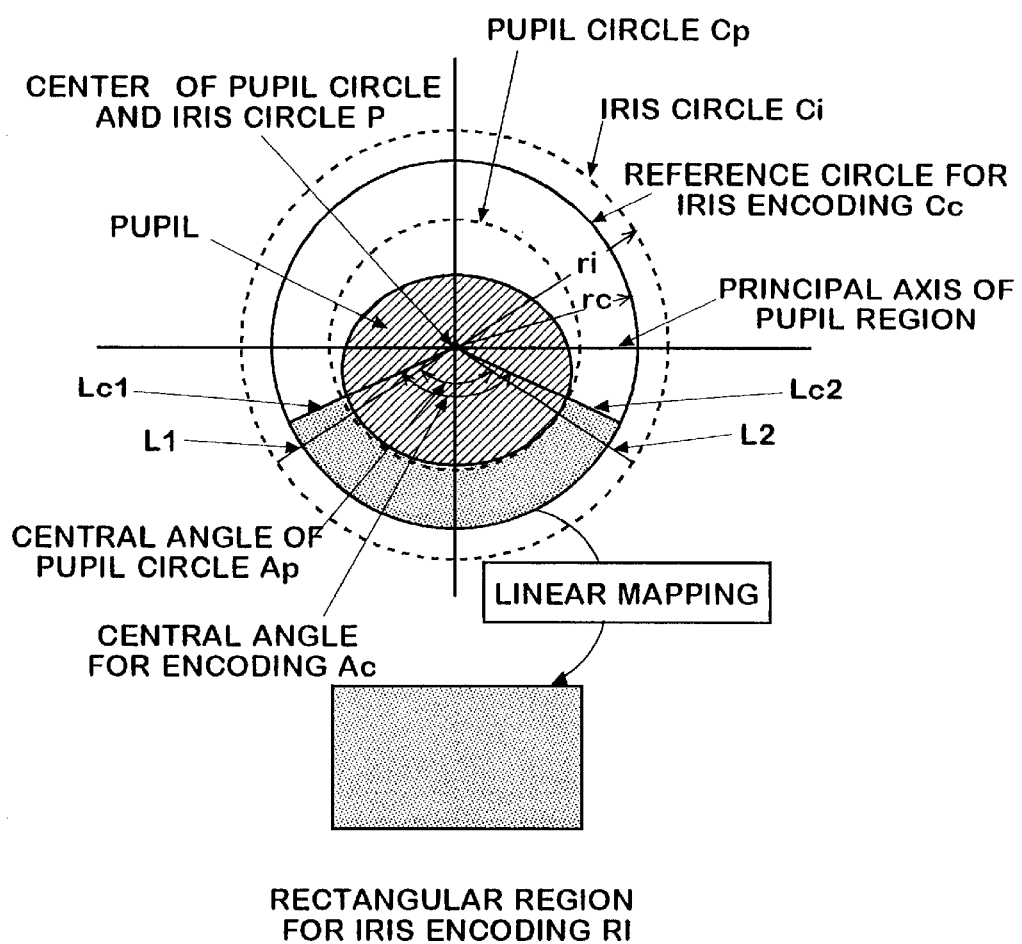
FIG. 14 is a view explaining the process of obtaining a rectangular shape for iris encoding of the first embodiment.

FIG. 14 is a view explaining processing of obtaining rectangular region for iris encoding (Step S105).

The iris code is produced for a region obtained by linearly mapping a system of polar coordinates having a center P of the pupil circle Cp as an origin on the x–y coordinate system. As shown in FIG. 14, to absorb an error in application of coordinates in the direction of a circumference, an angle obtained by giving a margin da to a central angle Ap of the pupil is used as a reference angle Ac for encoding. Because the lower portion of the iris hides behind the eyelid in some cases, the reference circle Cc for iris encoding is set so that the relation of the radius is rp<rc<ri.

The rectangular region RI for iris coding which is a rectangular data used to produce an iris code is obtained by linearly mapping a region surrounded by the reference circle Cc for iris encoding, the pupil circle, Lc1 and Lc2 shown in FIG. 14. In the description hereafter, the size (width x height) of the rectangular region RI for iris encoding is defined to be "rw×rh".

(5) Description of Processing of Producing Iris Codes (Step S106)

The size of the known 2-D Gabor filter is set to gw×gh, the length of a cord to LA, and the number of divisions along the direction (upward and downward direction in the drawing) of a radius of an iris to NA.

If the size of the filtering rectangular region is set to iw×ih, the following equations are obtained:

$$iw=LA+gw$$

$$ih=NA\times gh$$

(To calculate a convolution at a point, because information on an area with a width of ±gw/2 in front and in rear, iw is obtained by adding LA to gw.)

By cutting out the filtering rectangular region from the rectangular region RI for iris coding, the iris code is produced.

Figure 15:
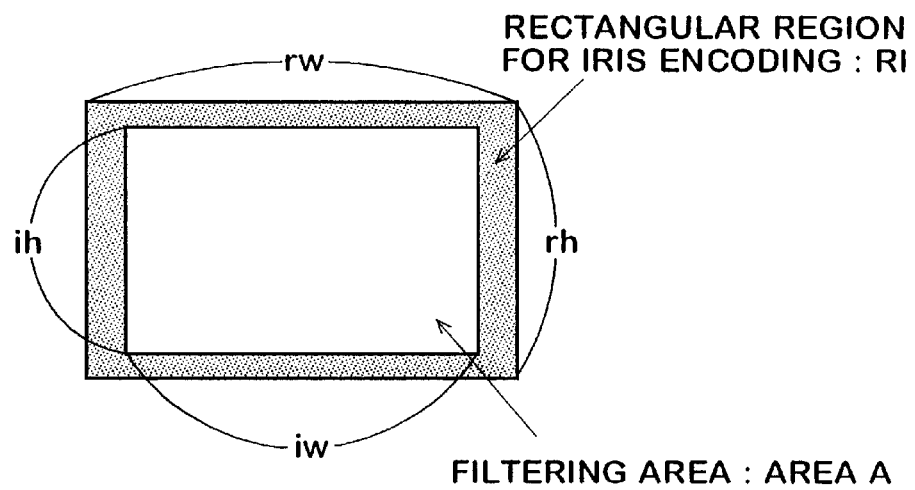
FIG. 15 is a view explaining the process of producing iris code of the first embodiment.
Figure 15:
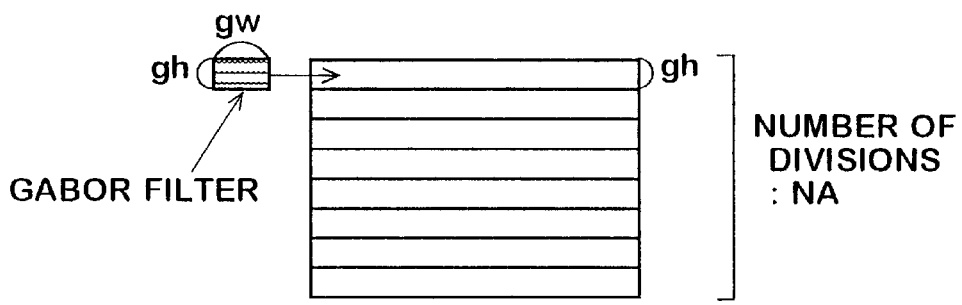

In FIG. 15, an example is shown when NA=8. The filtering is performed (i.e., the convolution is calculated) in the direction as shown in FIG. 15(b) to obtain a system of 0 (zero) or 1 as shown in FIG. 15(c). The iris codes obtained here constitutes iris codes along the direction of the circumference of the iris.

(6) Description of Processing of Comparing Iris Codes (Step S107)

The Hamming distance between iris codes already registered in advance in the registered code storing section 108 and those produced using inputted images is computed and the personal identification is authenticated. This processing is the same as in the case of the conventional one.

Moreover, in the above description, the area in which the iris code is produced is limited to the lower portion of the pupil, however, the area may contain the upper, lower, right and left regions, or the upper portion of the pupil may be used as the encoded area by symmetrically moving the pupil circle and iris circle around the center of the main axis of the pupil region.

This method of setting the system of coordinates may be applied not only to a plant-eating animal such as a horse or cattle but also to other animals including a dog, cat and to a human. For example, in the case of the cat the pupil of which is long lengthways, by rotating the image by 90 degrees or using each parameter with its value deviated by 90 degrees, this method may be used. Furthermore, the method of estimating the iris circle may be used even when the border between the sclera and the iris is seen.

As described above, according to the individual identification device of the present invention, by applying part of the circle to the contour of the pupil, by obtaining the contour line outside the iris region by the angle formed by two straight lines, one to connect both ends of the pupil and the other to pass the center of the circle to determine the iris region and to use it for individual identification, even if the shape of the pupil or the iris cannot be approximated using a circle as in the case of a horse or cattle having a non-circular pupil or iris, individual identification by using the iris is made possible. Moreover, even if the outer side of the iris hides behind the eyelid, the stable application of a system of coordinates for encoding is carried out.

Second Embodiment according to a second embodiment of the present invention, the individual identification device is so configured that two codes are produced in two directions in an image obtained and checking is made on the basis of these two codes.

Figure 16:
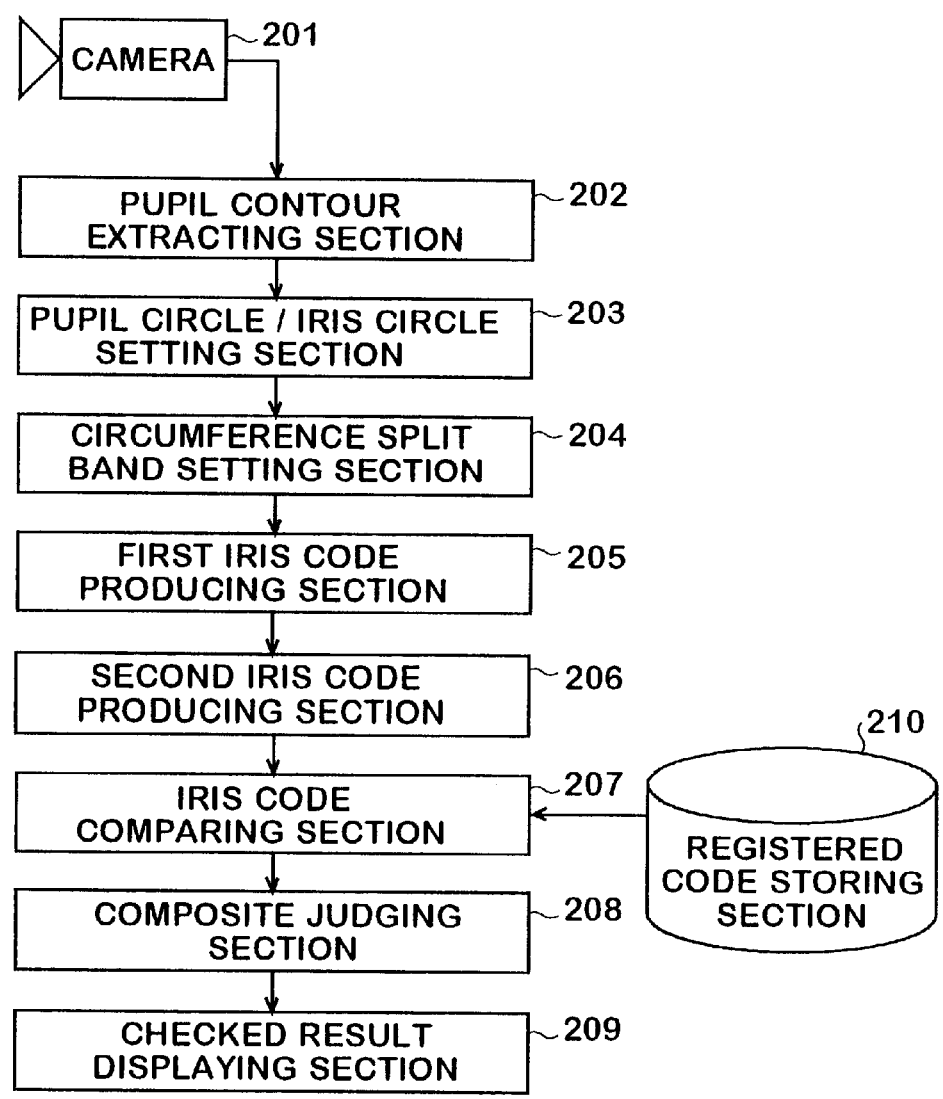
FIG. 16 is a block diagram explaining configurations of an individual identification device according to a second embodiment of the present invention.

FIG. 16 is a block diagram explaining configurations of an individual identification device according to the second embodiment of the present invention.

The individual identification device is comprised of a camera 201, a pupil contour extracting section 202, a pupil circle/iris circle setting section 203, a circumference split band setting section 204, a first iris code producing section 205, a second iris code producing section 206, an iris code comparing section 207, a composite judging section 208, a checked result displaying section 209 and a registered code storing section 210.

The components from the camera 201 to the circumference split band setting section 204 of the second embodiment are the same as in the first embodiment and their description is omitted accordingly.

The first iris code producing section 205 is a functional section to encode an image obtained by the circumference split band setting section 204 using a frequency filter. The second iris code producing section 206 is a functional section to produce codes in the direction orthogonal to the first iris code producing section 205, from an image obtained by the circumference split band setting section 204 using the frequency filter.

The iris code comparing section 207 is a functional section to compare iris codes produced by the first and second iris code producing sections 205 and 206 with those registered in advance. The composite judging section 208 is adapted to compositely judge results from the comparison of the two iris codes resulting from the iris code comparing section 207 with registered codes. The checked result displaying section 209 is a device to judge whether an image of an eye inputted according to results fed by the composite judging section conforms to that registered and to display it. The registered code storing section 210 is a functional section to store iris codes registered in advance using components including the camera 201 to the second iris code producing section 206.

Figure 17:
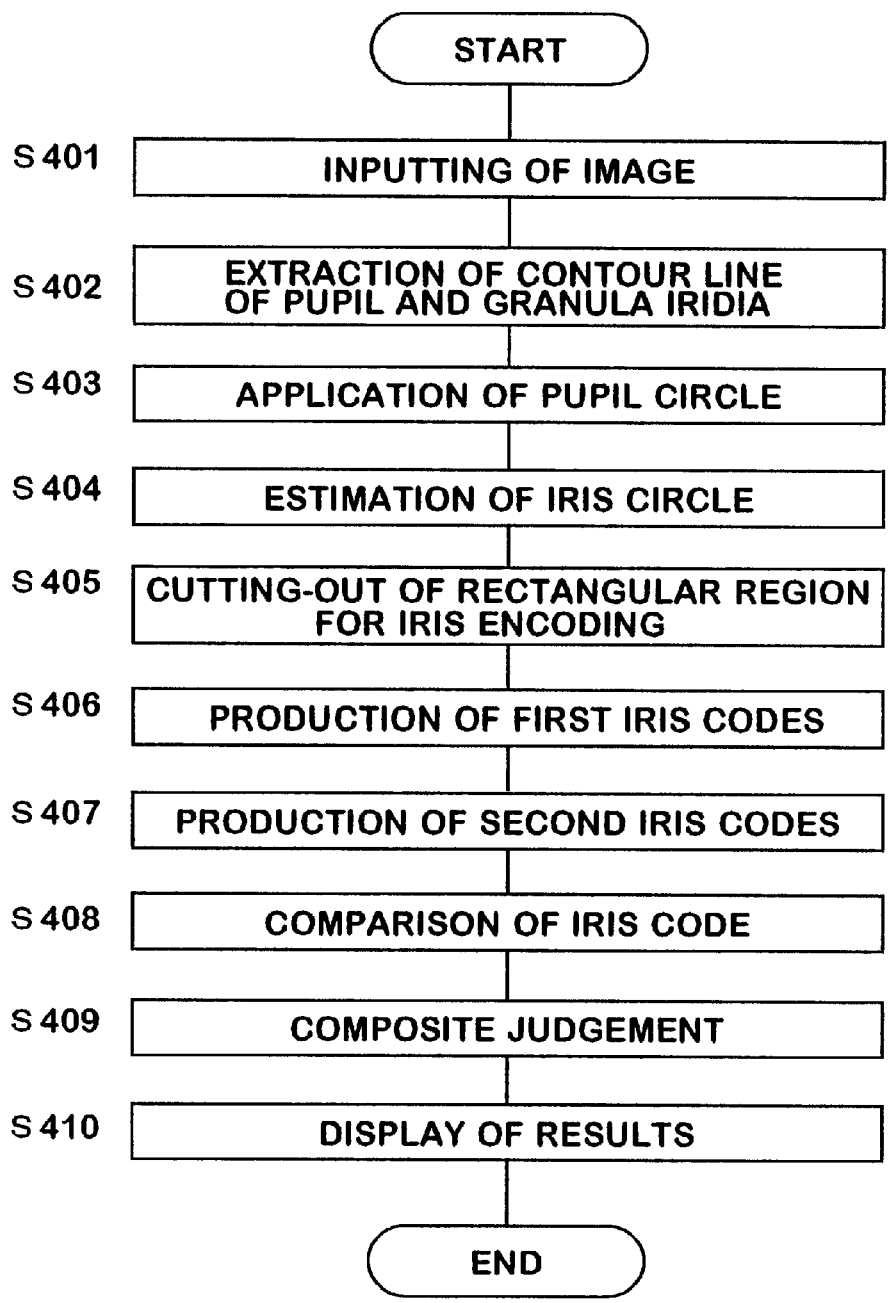
FIG. 17 is a flow chart showing operations of the individual identification device according to the second embodiment.

FIG. 17 is a flow chart showing operations of the individual identification device according to the second embodiment.

The Steps S401 to S405 of the second embodiment shown in FIG. 17 are the same as the Steps S101 to S105.

In Step S406, the first iris code producing section 205 splits the rectangular region and encodes each of split bands using a 2-D Gabor filter or the like to obtain a first iris code.

In Step S407, the second iris code producing section 206 splits the rectangular region in the direction orthogonal to the direction along which the rectangular region is split in the above Step S406 and encodes each of the split bands using the 2-D Gabor filters or the like to obtain a second iris code.

In Step S408, the iris code comparing section 207 compares iris codes produced above with those registered in advance and determines the degree of the dissimilarities between the two iris codes.

In Step S409, the composite judging section 208 judges compositely the results from the Step S408 and authenticates individual identification.

In Step S410, the checked result displaying section 209 displays the results from the Step S409.

In Step S406 described above, the direction for splitting the first iris code is the same as that in the first embodiment. This direction represents a line existing along the direction of an angle of a system of polar coordinates on the image inputted and, as in the conventional device, it also represents a line cut in a ring-shaped band on the border between the inside and the outside portions of the iris.

(1) Description of Processing of Producing Second Iris Code (Step S407)

Figure 18:
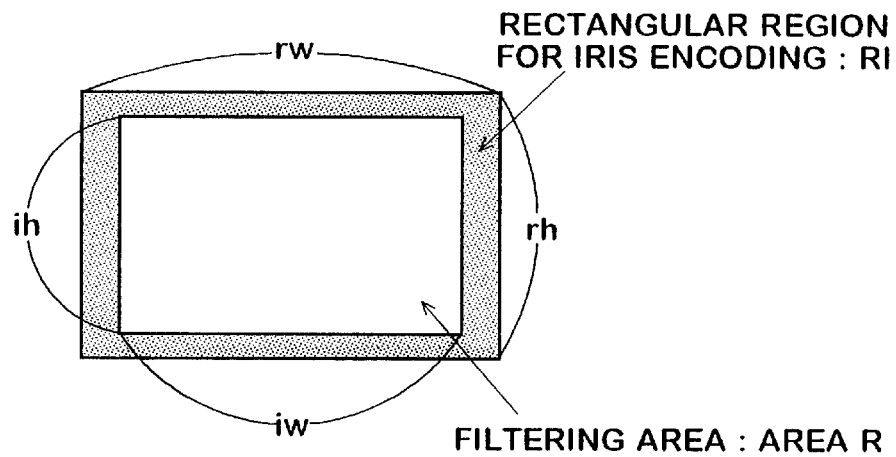
FIG. 18 is a view explaining the process of producing a second iris code of the second embodiment.
Figure 18:
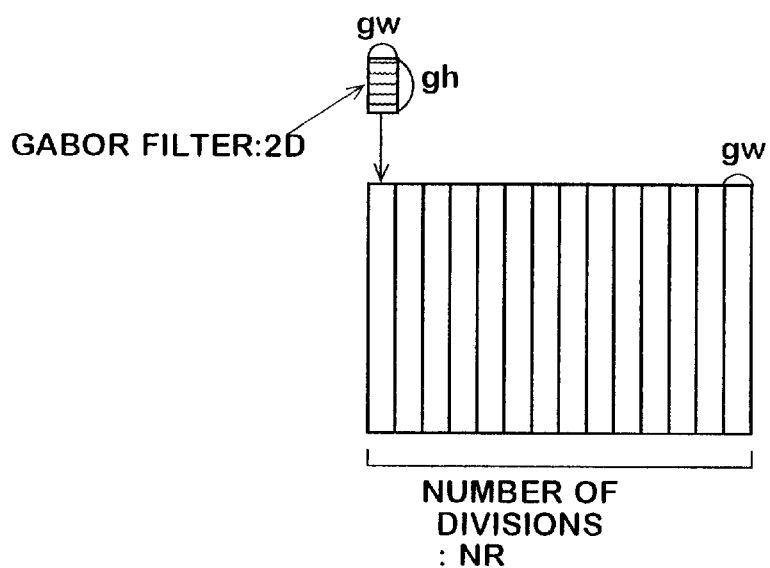

FIG. 18 is a view explaining the processing of producing second iris code (Step S407) of the second embodiment.

The size of the known 2-D Gabor filter is set to gw×gh, the length of a cord to LR, and the number of divisions to NR.

The direction of the division is a vertical direction. This direction represents a line existing along the direction of a radius of a system of polar coordinates on the image inputted and it also represents a line cut in a direction vertical to the direction along the circumference on the border between the inside and the outside portions of the iris (the direction of the first iris code). Moreover, the direction of a wave detected by the 2-D Gabor filter is orthogonal to the direction of the first iris code produced.

If the size of the filtering rectangular region is set to iw×ih, the following equations are obtained:

$$iw = NR \times gw$$

$$ih = LR + gh$$

(To calculate a convolution at a point, because information on an area with a width of ±gh/2 in its upper and lower areas, ih is obtained by adding LR to gh.)

By cutting out the filtering rectangular region from the rectangular region RI for iris coding, the iris code is produced.

In FIG. 18, an example is shown when NR=14. The filtering is performed (i.e., the convolution is calculated) in the direction as shown in FIG. 18(b) to obtain a system of 0 (zero) or 1 as shown in FIG. 18(c).

(2) Description of Processing of Comparing Iris Codes (Step S409)

A comparison with registered codes created in advance by processing including the Step S401 to S408 is performed. Assuming that the registered codes contains both the first and second iris codes, the comparison between the first iris codes or the second iris codes is performed by the conventional methods. The comparison of codes results in outputting of two pieces of information on the degree of the dissimilarities between the inputted iris codes and the registered iris codes (Hamming distance).

The degrees of the dissimilarities between the inputted iris code and the registered iris code of the first iris code and between inputted iris code and registered iris code of the second iris code are defined to be D1 and D2 respectively.

Whether the inputted image of an eye of an animal conforms to that registered is judged using the following criteria for judgement:

Criterion 1: D1 is smaller than a predetermined threshold value T1.

Criterion 2: D2 is smaller than a predetermined threshold value T2.

Criterion 3: Composite distance Ds of D1 and D2 is smaller than a predetermined threshold value Ts.

Method for determining the threshold values T1 and T2 to be used for the judgement by the criteria 1 and 2 and their method for judgement are the same as the conventional ones. On the other hand, the composite distance Ds of D1 and D2 to be used for the judgement using the criterion 3 are obtained by determining in advance (1) the distribution of D1 and D2 of things in themselves and (2) the distribution of D1 and D2 of other things and then plot them on a two-dimensional plane.

Figure 19:
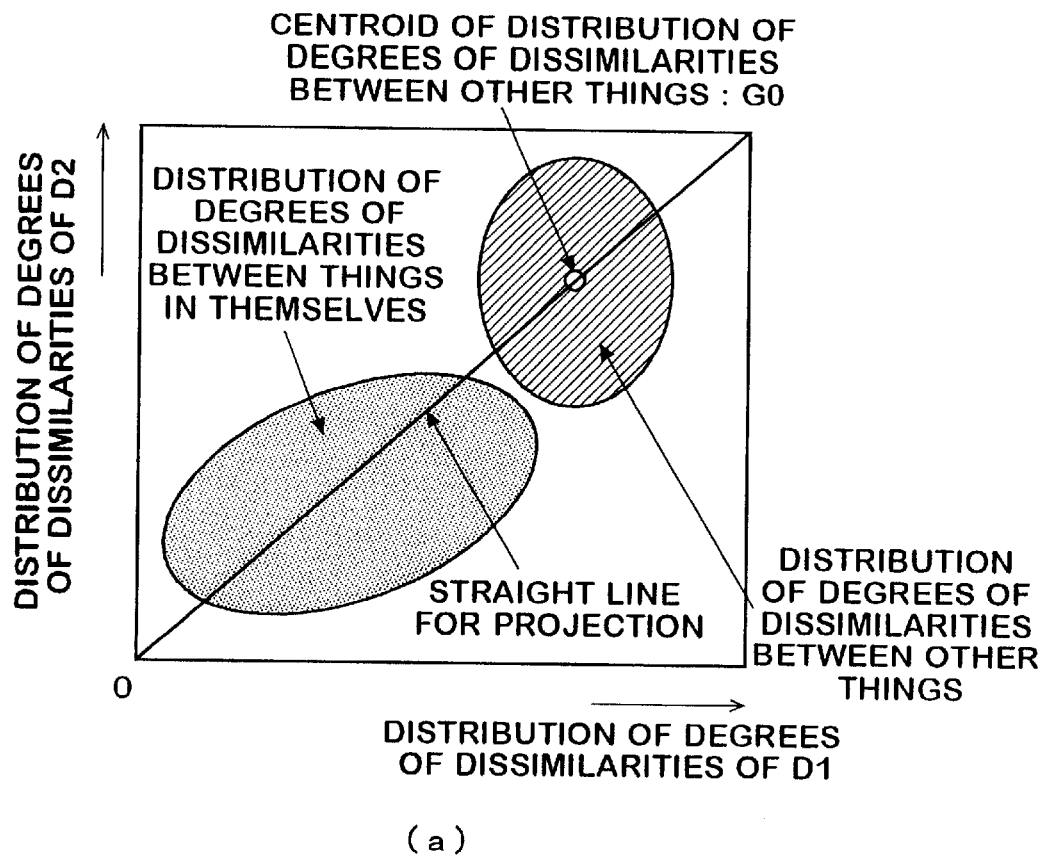
FIG. 19 is an explanatory view of distribution of degrees of dissimilarities.
Figure 19:
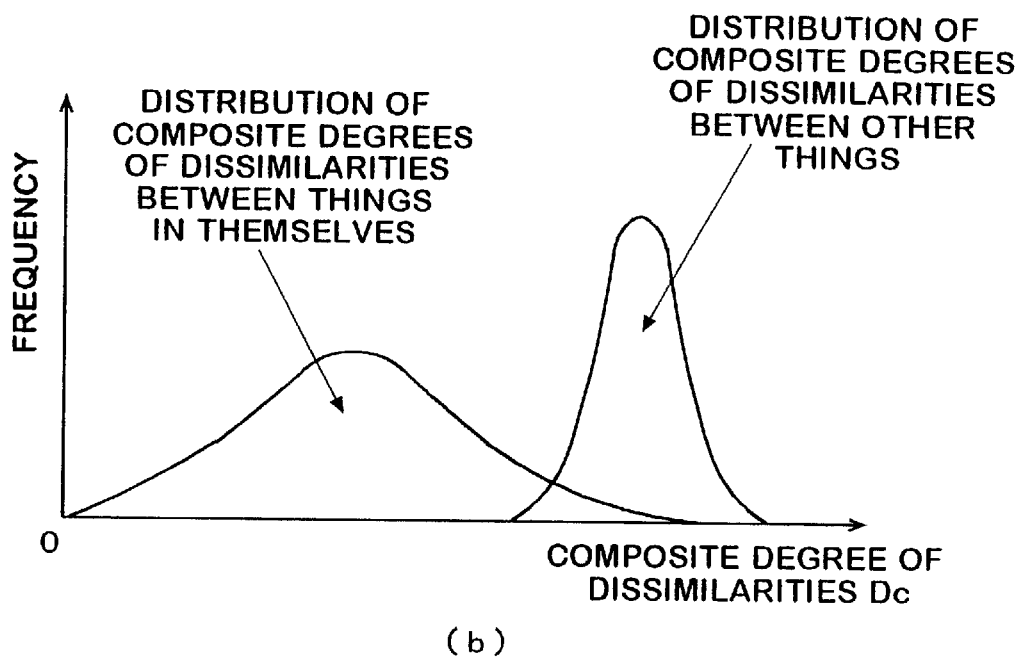

In FIG. 19(a), D1 is plotted on an axis of abscissas (x axis) and D2 is plotted on an axis of ordinates (y axis). From this drawing, centroid G0 of the distribution of other things is obtained and all points shown in FIG. 19(a) are projected onto a straight line connecting an origin with the centroid G0 (see FIG. 19(b)).

The distance from the origin is the composite distance Ds of D1 and D2 and, by using this distance, the threshold value used to distinguish things in themselves from other things is set. The equation of the straight line is stored. The composite distance Ds of D1 and D2 for an image inputted hereafter is computed using this stored equation in the same manner as above and whether a newly inputted image of an eye conforms to the eye image registered for an animal is judged.

The straight line that can be used for the projection may include the following:

A straight line connecting a centroid of the distribution of things in themselves with an origin.

A principal axis used when principal component analysis on the distribution of things in themselves.

A principal axis used when principal component analysis on the distribution of other things.

Single judgement result obtained by using the criteria 1 to 3 can be used as a judgement result for the whole system. The judgement result obtained by using the criterion 3 can be also used as a judgement result for the whole system.

Moreover, instead of the judgement method using the criterion 3, other methods, if only they can be used for classifying two patterns on the two-dimensional plane such as a pattern matching, may be applicable.

According to the second embodiment, the method for producing two iris codes may be applied not only to a horse or cattle but also other animals including a dog or cat and a human. It is apparent that this method is applicable not only to animals but also humans and personal identification can be authenticated by using two iris codes with high accuracy.

As described above, according to the method for extracting the iris region of the second embodiment, since two iris codes are obtained by dividing the iris region in the two directions, one along a circumference and the other orthogonal to the circumference and performing the image processing on each of the divided bands to encode the image, two pieces of characteristic data can be obtained from one image of the iris region. Furthermore, according to the individual identification device of the second embodiment, since patterns in two directions are analyzed for checking, more accurate checked results can be obtained compared with the case where a pattern in one direction is analyzed.

It is apparent that the present invention is not limited to the above embodiments but may be changed and modified without departing from the scope and spirit of the invention.

What is claimed is:

1. A method for extracting an iris region from an eye image obtained by taking a picture of an individual comprising steps of:

applying a first circular arc to part of a border line between a pupil region and the iris region contained in said eye image; and setting a contour line outside said iris region on a second circular arc having the same center as said first circular arc;

wherein a radius of said second circular arc being associated with a central angle of said first circular arc is estimated based on said central angle and a radius of said first circular arc.

2. The method for extracting an iris region according to claim 1, wherein said iris region is split in two directions, one being along said first circular arc and the other being orthogonal to said first circular arc, and wherein predetermined image processing is performed on each split band for encoding and obtaining two iris codes.

3. The method for extracting an iris region according to claim 1, further comprising the step of:

establishing a reference circle concentric with said first circular arc and said second circular arc, the radius of said reference circle being greater than a radius of said first circular arc and less than a radius of said second circular arc.

4. The method for extracting an iris region according to claim 3, further comprising the steps of:

mapping a region defined by a central angle of said first circular arc and lying between said first circular arc and said reference circle to a rectangular region; and performing iris encoding on said rectangular region.

5. An individual identification device comprising:

a pupil contour extracting means to extract a contour of a pupil region from an eye image obtained by taking a picture of an individual, said pupil contour extracting means comprising:

means for extracting a rectangular region containing the pupil region from the eye image; and means for performing image processing on said rectangular region to extract said contour;

a pupil circle/iris circle setting means to apply a circular arc to part of said extracted by said pupil contour extracting means and to obtain a border line outside said iris region based on a central angle of said circular arc;

an iris code producing means to produce an iris code of said iris region set by said pupil circle/iris circle setting means; and an iris code comparing means to compare said iris code produced by said iris code producing means with an iris code registered in advance and to use the result for individual identification of said eye image.

6. The individual identification device according to claim 5, wherein said means for performing predetermined image processing comprises:

first binarization-processing means for obtaining a pupil contour; and second binarization-processing means for obtaining a combined pupil and granula iridia contour.

7. The individual identification device according to claim 5, wherein said means for performing predetermined image processing further comprises:

means for computing a centroid and principal axis of said pupil; and means for correcting an inclination of said pupil.

8. An individual identification device comprising:

a pupil contour extracting means to extract a contour of a pupil region from an eye image obtained by taking a picture of an individual;

a pupil circle/iris circle setting means to apply a circular arc to part of a contour of a pupil region extracted by said pupil contour extracting means and to obtain a border line outside said iris region based on a central angle of said circular arc;

a first iris code producing means to produce said iris code of said iris region set by said pupil circle/iris circle setting means along the direction of a circumference of said iris region;

a second iris code producing means to produce said iris code of said iris region set by said pupil circle/iris circle setting means along the direction being orthogonal to said circumference; and an iris code comparing means to compare two iris codes produced by said first and second iris code producing means with an iris code registered in advance and to use the result for individual identification of said eye image.

9. The individual identification device according to claim 8, wherein said iris code comparing means outputs two degrees of dissimilarities between said produced iris codes and said registered iris code, and wherein said device further comprises a composite judging means to obtain a composite degree of dissimilarity from said two degrees of dissimilarities and to obtain said result for individual identification of said eye image based on said composite degree of dissimilarity.

10. A method for extracting an iris region from an eye image in order to identify the being whose eye corresponds to said eye image, said eye image containing a pupil portion that may be non-circular, comprising the steps of:

getting a border line between said pupil portion and an iris portion contained in said eye image;

establishing an arc fitting a part of said border line and serving as a part of a hypothetical pupil circle;

finding a center of said hypothetical pupil circle containing said arc;

establishing an iris extraction-use circle which is concentric with said center and has a radius bigger than that of said hypothetical pupil circle;

acquiring an iris region to be extracted, said iris region to be extracted being defined at least by said arc and an outer arc being a part of said iris extraction-use circle and corresponding to said arc; and judging an iris circle corresponding to said arc by using a graph indicating a predetermined corresponding relationship between possible arcs and possible iris circles, wherein said iris extraction-use circle is established using the judged iris circle.

11. The method for extracting an iris region according to claim 10, wherein said iris extraction-use circle is established as a standard circle having a radius smaller than that of the judged iris circle.

12. The method for extracting an iris region according to claim 10, wherein said arc is formed from a part of either a circle or an ellipse, and wherein said iris extraction-use circle is formed from either a circle or an ellipse.

13. A method for extracting an iris region from an eye image in order to identify the being whose eye corresponds to said eye image, said eye image containing a pupil portion that may be non-circular, comprising the steps of:

getting a border line between said pupil portion and an iris portion contained in said eye image;

establishing an arc fitting a part of said border line and serving as a part of a hypothetical pupil circle;

finding a center of said hypothetical pupil circle containing said arc;

establishing an iris extraction-use circle which is concentric with said center and has a radius bigger than that of said hypothetical pupil circle; and acquiring an iris region to be extracted, said iris region to be extracted being defined at least by said arc and an outer arc being a part of said iris extraction-use circle and corresponding to said arc, wherein said step of getting a border line comprises the step of:

binarization-processing said eye image using a threshold value which, considering lower density values to represent darker color, is bigger than a color average density of said pupil portion but is smaller than a color average density of said iris portion.

14. An individual identification device for identifying an animal based on an eye image of the animal, said eye image having a pupil region that may be non-circular, by extracting an iris region from said eye image, the device comprising:

a pupil contour extracting section for getting a border line between said pupil portion and an iris portion contained in said eye image;

a pupil circle/iris circle setting section for establishing an arc fitting a part of said border line and serving as a part of a hypothetical pupil circle, for finding a center of said hypothetical pupil circle containing said arc, and for establishing a iris extraction-use circle which is concentric with said center and has a radius bigger than that of said hypothetical pupil circle;

a circumference split band setting section for setting up an iris region to be extracted, said iris region being defined at least by said arc and an outer arc being a part of said iris extraction-use circle and corresponding to said arc.

15. The individual identification device according to claim 14, wherein said pupil circle/iris circle setting section judges an iris circle corresponding to said arc by using a graph indicating a predetermined corresponding relationship between possible arcs and possible iris circles and uses the judged iris circle to establish said iris extraction-use circle.

16. The individual identification device according to claim 15, wherein said iris extraction-use circle is established as a standard circle having a radius smaller than that of the judged iris circle.

17. The individual identification device according to claim 14, wherein said pupil contour extracting section obtains said border line by binarization-processing said eye image using a threshold value which, considering lower density values to represent darker color, is bigger than a color average density of said pupil portion but is smaller than a color average density of said iris portion.

* * * * *